United States Patent [19]

Perez, Jr.

[11] Patent Number: 4,597,382

[45] Date of Patent: Jul. 1, 1986

[54] MEDICAL SPECULUM AND PROCEDURE

[76] Inventor: Raul Perez, Jr., 109 Woodlawn Rd., Monroe, Conn. 06468

[21] Appl. No.: 590,432

[22] Filed: Mar. 16, 1984

[51] Int. Cl.<sup>4</sup> .............................................. A61B 1/32
[52] U.S. Cl. .................................. 128/17; 128/303.1
[58] Field of Search ........................ 128/17, 18, 303.1

[56] References Cited

U.S. PATENT DOCUMENTS

| | | | |
|---|---|---|---|
| 3,762,400 | 10/1973 | McDonald | 128/18 |
| 3,841,317 | 10/1974 | Awais | 128/17 |
| 3,851,642 | 12/1974 | McDonald | 128/18 |
| 4,249,533 | 2/1981 | Komiya | 128/303.1 |
| 4,492,220 | 1/1985 | Hayes | 128/17 |
| 4,520,814 | 6/1985 | Weeks | 128/303.1 |

FOREIGN PATENT DOCUMENTS 73366  5/1983  Japan ................. 128/303.1

OTHER PUBLICATIONS

"Carbon Dioxide Laser Surgery of Larynx," New York State Journal of Medicine, Jul., 1975, pp. 1235–1236, by Olivero, M.D. and Fermon, M.D.

Primary Examiner—William H. Grieb
Attorney, Agent, or Firm—Frank J. Thompson

[57] ABSTRACT

A sleeve shaped body having a liquid absorbent segment and a wettable segment is positioned on a speculum member during a medical procedure in which a laser instrument is utilized. The liquid absorbent segment inhibits reflection and dissipates the energy of any errant, impinging laser beams. Placement in a body cavity of the speculum with the sleeve shaped body positioned thereon is facilitated by use of the wettable segment which provides for a relatively low sliding friction in contact with human body tissue. A method using this technique is described.

23 Claims, 6 Drawing Figures

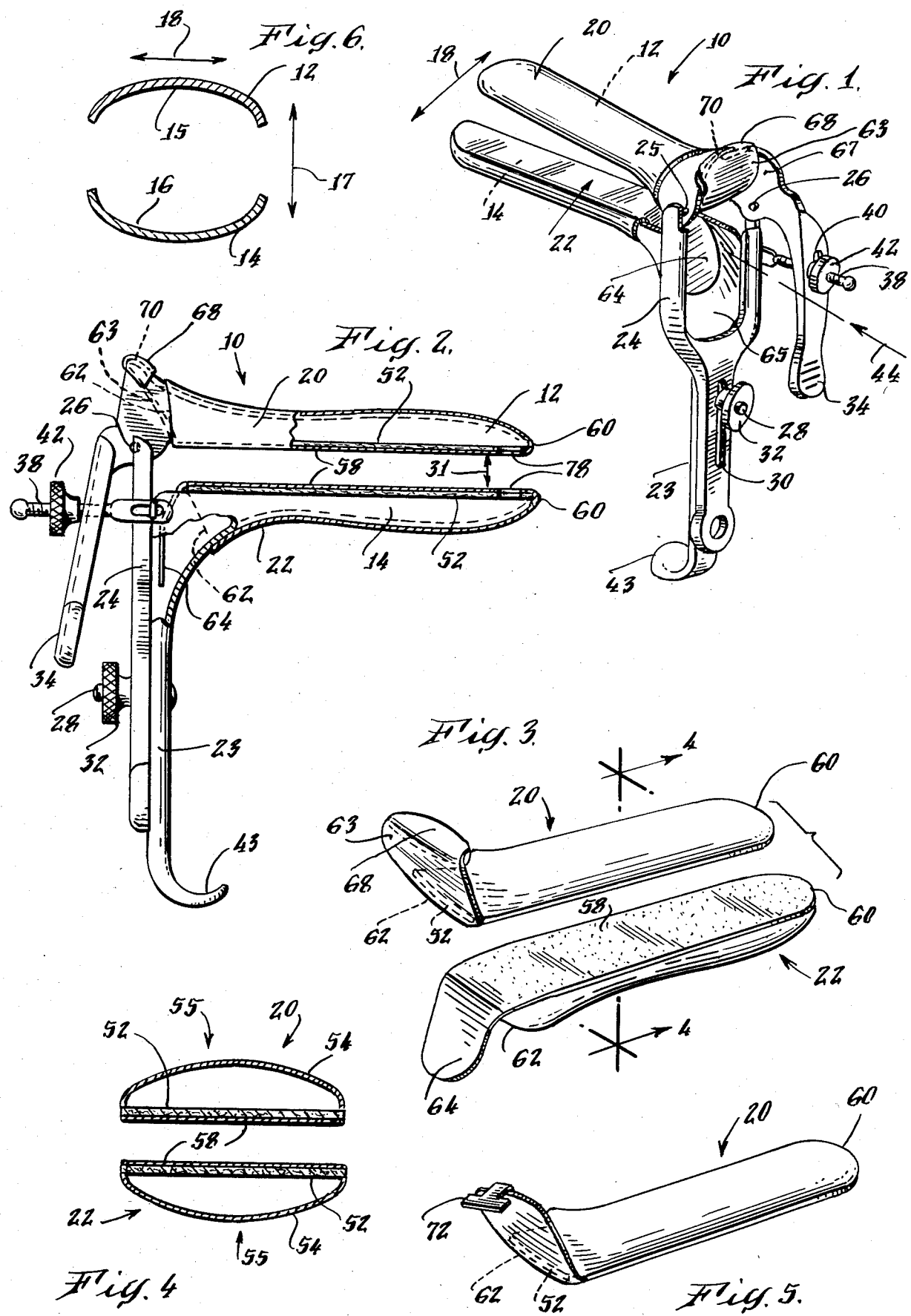

MEDICAL SPECULUM AND PROCEDURE

BACKGROUND OF THE INVENTION

1. Field of the Invention

This invention relates to an improved gynecological procedure and apparatus for use in the procedure. The invention relates more particularly to a gynecological surgical procedure utilizing a laser instrument.

2. Description of the Prior Art

A medical speculum, as is known, is an apparatus having a pair of elongated members which are placed in a body cavity and which are relatively adjustable after positioning in the body cavity so as to provide access to the body cavity during a medical procedure. One such procedure is a surgical procedure performed with a laser instrument. The laser instrument projects a narrow, intense beam of radiant energy between the speculum members into the cavity. During the procedure, the laser is manipulated by the medical practitioner to cause impingement of the beam on body tissue being treated.

At times, the laser beam may undesirably impinge upon and damage body tissue other than the tissue being treated. This can happen, for example, during manipulation of the laser beam if the beam errantly impinges upon the speculum. Generally, the speculum is fabricated of stainless steel which presents a reflective surface to the beam. A laser beam striking the speculum can thus be uncontrollably reflected into the body cavity. In addition, the beam which errantly impinges the speculum may also be reflected outwardly from the body cavity and create a potential danger for attending medical personnel.

A single use, disposable speculum fabricated of a polymer plastic has been used which does not exhibit the relatively high degree of reflectivity of the stainless steel. However, over the course of a number of medical procedures, the number of disposable speculums required becomes relatively expensive in comparison with the reusable metal speculum. Moreover, impingemeht of a laser beam on the plastic speculum softens, burns and deforms the speculum in the area of impingement and creates undesired and potentially toxic vapors in the body cavity. It has also been proposed to roughen the metal speculum surface in order to reduce reflectivity. This approach, however, merely reduces the degree of reflection and does not eliminate potentially harmful reflections. A further proposal to coat the metal speculum with a plastic material is highly costly since the speculum is not reusable due to the impracticability of sterilizing the coated speculum in an autoclave without damage to the coating.

SUMMARY OF THE INVENTION

Accordingly, it is an object of this invention to provide an improved speculum for use in a laser surgical procedure.

Another object of the invention is to provide an improved speculum which inhibits reflection of a laser beam.

Another object of the invention is to provide an improved speculum which dissipates the energy of a laser beam.

A further object of the invention is to provide a reusable speculum which is adapted to inhibit reflection and to dissipate the energy of a laser beam impinging thereon.

Another object of the invention is to provide a disposable body for use with a speculum which inhibits reflection and absorbs the energy of an impinging laser beam.

Another object of the invention is to provide an improved gynecological medical procedure utilizing a laser beam.

In accordance with features of the invention, an improved speculum comprises first and second generally parallel, longitudinaly extending members. The speculum also includes a means which intercouples the members and adjusts their relative spatial position for restraining the members in fixed relative spatial positions. A disposable body of liquid absorbent material is positioned on at least one of the members. A means is also provided for retaining the disposable body on the member. Upon impingement by a laser beam on the wetted disposable body, the energy in the laser beam is dissipated thereby inhibiting reflection and avoiding undesired damage to body tissue not being treated.

In accordance with more particular features of the invention, the disposable liquid absorbent body has a sleeve-shaped configuration which is adapted to be positioned about and to receive the speculum member thus restraining the body on the member. The sleeve-shaped body includes a first, liquid-absorbent segment which when wetted retains a liquid, and, a second segment which when wetted provides relatively low-friction sliding contact with body tissue. The wetted liquid absorbent segment dissipates laser beam energy impinging upon the member while the wetted second segment provides relatively low-friction sliding contact with body tissue and thus facilitates placement and entry of the speculum into the body cavity.

The medical procedure of this invention comprises positioning a sleeve-shaped body having a liquid absorbent segment and a wettable surface segment on a first member of a speculum having two longitudinally extending members; wetting the body with a liquid which it retains; placing the speculum in a body cavity; adjusting the speculum members to establish spatial relation therebetween; and, projecting a laser beam between the speculum members and toward body tissue which is to be treated. Undesired projection of the laser beam at the speculum member results in impingement of the beam on the absorbent body which inhibits reflection of the beam and dissipates the laser radiant energy. The procedure further provides for removal of the speculum from the body cavity and disposing of the sleeve-shaped body.

BRIEF DESCRIPTION OF THE DRAWINGS

These and other objects and features of the invention will become apparent with reference to the following specification and the drawing wherein:

FIG. 1 is a perspective view of a speculum constructed in accordance with features of the invention and which is used with the method of this invention;

FIG. 2 is a side elevation view partly broken away and partly in section of the speculum of FIG. 1;

FIG. 3 is a perspective view of liquid absorbent bodies used with the speculum of FIG. 1;

FIG. 4 is a view taken along line 4—4 of FIG. 3;

FIG. 5 is a perspective view of an alternative embodiment of a liquid absorbent body in accordance with the invention; and, FIG. 6 is a fragmentary, cross section view of members of a medical speculum.

DETAILED DESCRIPTION

Referring now to the drawing, there is illustrated a medical speculum 10 having a first, upper, elongated, longitudinally extending member 12, and, a second, lower, elongated, longitudinally extending member 14. The members 12 and 14 extend generally parallel as best illustrated in FIG. 2. Each of these members 12 and 14 has a concave surface 15,16 respectively (FIG. 6) extending toward each other in a direction 17 and which also extends in a direction 18 transverse to the member's length. The members 12, 14 of FIG. 1 and 2 have supported thereon bodies 20 and 22 respectively which when wetted are adapted to dissipate radiant energy impinging thereon. These bodies are described in further detail hereinafter.

A means is provided for intercoupling the members 12 and 14 in order to vary their relative spatial positions and to lock and maintain the members in a selected orientation. This means includes a handle segment 23 which is integrally formed with the member 14 and a yoke-shaped member 24 which is coupled to the member 12 by pivot pins 25 and 26. A screw 28, which is mounted to the member 23, extends through a slot 30 in the member 24. A knurled nut 32 engages the screw 28 for locking the members 23 and 24 in fixed relative positions. The members 23 and 24 can be adjusted to vary the spaced apart distances of the generally parallel members 12 and 14. This spaced apart distance is represented by reference line 31 in FIG. 2.

The foregoing means further includes an adjusting arm 34 which is integrally formed with the member 12 and which extends from a rear segment thereof. By pressing arm 34, the member 12 is pivotally rotated on pivot pins 25 and 26 relative to the member 14. A screw 38 which is mounted to the yoke member 24 extends through an aperture 40 in the arm 34 and is engaged by a knurled nut 42 thereby restraining the member 12 in a fixed spatial relationship with respect to the member 14. The speculum is formed of stainless steel which can be sterilized and is thus reusable.

In use, the physician places the speculum 10 in a body cavity and adjusts the spatial positions of the members 12 and 14 by varying the positions of members 23 and 24 and by adjusting the lever arm 34. Movement of the speculum is restrained by a curved lip 43 which is integrally formed with the member 23 and which engages the patient's body.

The speculum 10 is used in a medical procedure in which a laser light beam indicated by reference numeral 44 in FIG. 1 is manipulated by a medical practioner and is projected into a body cavity between the members 12 and 14. This beam 44 is a narrow intense beam which is projected so as to impinge on body tissue being treated. Treatment with a laser beam is effected by the highly concentrated, energy content of the beam. Body tissue comprises about 80% water and the medical procedure using a laser is accomplished through laser beam energy which rapidly evaporates the water content of the body tissue.

A medical practitioner is required to manipulate the laser beam 44 and project it between the relatively closely spaced members 12 and 14 toward the tissue under treatment in a body cavity. In view of the confined area of operation, the beam at times will undesirably impinge upon the reflecting metal surfaces 15 and 16 of the members 12 or 14, respectively. When this occurs, the beam is reflected out of its intended course and can impinge upon body tissue other than that intended to be treated, or, it may re-reflect several times between the surfaces 15 and 16 and exit rather than enter the body cavity. In the former case, the beam may damage other body tissue while in the latter case, it can endanger the attending medical personnel.

A disposable body 22 having a generally sleeve-shaped configuration is provided and is adapted to be positioned about and to receive the member 14 within the sleeve. The sleeve is readily placed on the member by sliding it on. As illustrated in FIG. 4, the sleeve includes a first, liquid absorbent segment 52 which is non-reflective to laser radiant energy and when wetted is adapted to absorb and to retain liquid. Segment 52 is fabricated of absorbent paper, cotton, terry cloth or other similar absorbent material. The sleeve also includes a second, wettable segment 54 having a surface 55 which when wetted exhibits relatively low sliding friction in contact with body tissue.

Segment 54 is fabricated of a polymer plastic which exhibits relatively low sliding friction with body tissue when wetted. Suitable materials include nylon, rayon, and vinyl. When segment 54 is substantially liquid impermeable, a liquid permeable segment 58 is positioned adjacent the segment 52 to permit wetting of segment 52. Segment 58 is non-reflective to laser radiant energy and is formed of woven or matted tissue, for example. Segments 52, 54 and 58 are assembled by heat sealing, stitching, or gluing the segments along their edges to provide a sleeve-shaped configuration which is closed at one end 60 and open at an opposite end 62. The sleeve-shaped body 20 which is positioned on member 12 is similarly constructed. Segments 54 and 58 of the bodies 20 and 22 face each other as illustrated in FIG. 4.

In practice, the speculum with bodies 20 and 22 positioned thereon will be wetted by dipping, for example, in water thereby soaking the liquid absorbent segment 52 and wetting the segment 54. The speculum is then positioned in a body cavity. The segment 54 is formed of a material which is wettable and which thus provides relatively low sliding frictional contact with body tissue as the speculum is placed in the body cavity. If the laser beam 44 is inadvertently directed at members 12 or 14 during the procedure, the beam will impinge upon the segment 58 and the liquid absorbent segment 52. The segments 58 and 52 are substantially nonreflective. Moreover, segment 52 will dissipate heat energy of the impinging laser beam. The energy of laser beam 44 impinging on the liquid soaked segment 52 will be dissipated in causing the liquid to vaporize. Thus, the bodies 20 and 22 inhibit potential injury by the laser beam during the medical procedure by inhibiting reflection and by dissipating energy of the beam.

In order to inhibit reflection from the speculum which can endanger attending medical personnel, the segments 52 and 58 of body 22 includes an extending flap 64 which extends over a lower and reflective metallic segment 65 of the member 14. If the beam 44 is misdirected at the member 14 in this area, it will impinge upon the flap 64 and will not be reflected. The upper body 20 also includes a similar segment 63 for inhibiting reflection of the beam from an upper outer surface 67 of the member 12. As illustrated in FIG. 2, the flap segment 63 of upper body 20 includes at a distal point, an integrally formed pocket 68. The pocket 68 extends outwardly about the member 12, engages an outer upper edge 70 and supports the flap 63 against the member 12. Alternatively, when the upper member 12 includes a slot, the flap 63 may include a tab segment 72 to position and retain the flap 63 adjacent the outer, upper member 12 for inhibiting reflection in the outer area.

In those instances in which a suction tube is utilized with a speculum, an aperture 78 can be formed in the segments 52 and 58 as illustrated in FIG. 2 to accommodate the tube.

There has thus been described an improved speculum, protective sleeve and method for a laser surgical procedure. The speculum includes a disposable body which inhibits reflection of a laser beam impinging thereon and dissipates energy of the beam. The body further includes means for reducing the friction of sliding contact between the body and human body tissue as the speculum is placed in a body cavity. The device and method are relatively economical and advantageous in that they protect both the patient and medical practitioner from injury by the laser beam.

While there has been described a particular embodiment of the invention, it will be apparent to those skilled in the art that variations may be made thereto without departing from the spirit of the invention and the scope of the appended claims.

What is claimed is:
1. An improved speculum comprising:
   a. first and second generally parallel, longitudinally extending members;
   b. means intercoupling said members for adjusting the relative spatial position therebetween and for restraining said members in fixed relative spatial positions;
   c. a disposable body positioned on at least one of said members;
   d. said body being nonreflective to radiant energy and adapted to dissipate impinging radiant energy when wetted; and,
   e. means for retaining said body on said member, whereby radiant energy projected between said members during a medical procedure and which impinges on said body is dissipated.
2. The speculum of claim 1 wherein each of said members extends transversely and is curved in a transverse direction.
3. The speculum of claim 1 wherein said first and second members are formed of a radiant energy reflective material.
4. The speculum of claim 1 wherein said disposable body has a configuration which provides for engagement between said body and said member for retaining said body on said member.
5. The speculum of claim 4 wherein said disposable body has a sleeve-shaped configuration and is adapted to be positioned about and to receive said member.
6. The speculum of claim 5 wherein said sleeve-shaped body is positioned on said first member and a second sleeve-shaped body is positioned on said second member.
7. The speculum of claim 6 wherein said second sleeve-shaped body includes a pocket segment for engaging a segment of said second member.
8. The speculum of claim 5 wherein said sleeve-shaped configuration is closed at one end thereof and open at a second opposite end thereof.
9. An improved speculum comprising:
   a. first and second generally, longitudinally extending members;
   b. means intercoupling said members for adjusting the relative spatial position therebetween and for restraining said members in fixed relative spatial positions;
   c. a disposable body positioned on at least one of said members;
   d. said disposable body having a sleeve shaped configuration which is adapted to be positioned about and to receive said member and thereby provide for engagement between said body and said member and retain said disposable body on said member;
   e. said body including a first liquid absorbent segment which is not reflective to radiant energy and is adapted to dissipate impinging radiant energy when wetted;
   f. said body including a second wettable segment which when wetted exhibits relatively low sliding friction in contact with body tissue; and
   g. means for retaining said body on said member, whereby radiant energy projected between said members during a medical procedure and which impinges on said body is dissipated.
10. The speculum of claim 9 wherein said sleeve-shaped body includes a flap segment extending longitudinally from said first segment.
11. The speculum of claim 9 wherein said liquid absorbent segment comprises an absorbent paper.
12. The speculum of claim 9 wherein said liquid absorbent segment comprises cotton.
13. The speculum of claim 9 wherein said second segment is formed of a polymer plastic material.
14. The speculum of claim 13 wherein said second segment comprises nylon.
15. The speculum of claim 9 wherein said first segment includes a first surface facing toward said second member and a second surface facing toward patient body tissue, said first and second segments of said sleeve-shaped body are positioned respectively adjacent said first and said second surfaces of said member.
16. The speculum of claim 9 including a liquid permeable segment positioned adjacent said first liquid absorbent segment.
17. A disposable body for use with a speculum having first and second longitudinally extending members, said body having a segment which is not reflective to laser radiant energy and which dissipates impinging laser radiant energy when said body is wetted, said body having a sleeve-shaped configuration which is adapted to be positioned on and to receive one of said speculum members for retention of said dispoable body thereon, said sleeve-shaped configuration including a first segment formed or a liquid absorbent material and a second segment formed of a wettable material which exhibits low sliding firction in contact with body tissue.
18. The disposable body of claim 12 wherein said body includes an extending flap segment.
19. The disposable body of claim 18 wherein said flap segment includes a pocket segment for engaging a member of said speculum.
20. The disposable body of claim 18 wherein said flap segment includes a tab segment for engaging a member of said speculum.
21. An improved surgical method comprising the steps of
   a. positioning a disposable sleeve-shaped body having a non-reflective, liquid absorbent segment and a wettable segment on a first member of a speculum having two longitudinally extending reflective members;

b. wetting the body;

c. positioning the speculum in a body cavity;

d. adjusting the speculum members to establish a spatial relation there between; and, e. projecting a laser beam between the speculum members toward body tissue in the body cavity which is to be treated.

22. The method of claim 21 wherein said body is wetted by placing in a liquid.

23. The method of claim 21 including the step of removing the speculum from the body cavity after treatment and disposing of said sleeve-shaped body.

* * * * *